(12) United States Patent
Nakabayashi et al.

(10) Patent No.: US 8,054,469 B2
(45) Date of Patent: Nov. 8, 2011

(54) OPTICAL PROBE AND OPTICAL TOMOGRAPHIC IMAGE PRODUCTION APPARATUS USING THE PROBE

(75) Inventors: Koki Nakabayashi, Ashigarakami-gun (JP); Tadashi Masuda, Ashigarakami-gun (JP)

(73) Assignees: FUJIFILM Corporation, Tokyo (JP); Fujinon Corporation, Saitama-Shi (JP)

( * ) Notice: Subject to any disclaimer, the term of this patent is extended or adjusted under 35 U.S.C. 154(b) by 158 days.

(21) Appl. No.: 12/391,872

(22) Filed: Feb. 24, 2009

(65) Prior Publication Data
US 2009/0213387 A1    Aug. 27, 2009

(30) Foreign Application Priority Data
Feb. 25, 2008    (JP) .................................. 2008-042604

(51) Int. Cl.
*G01B 9/02*    (2006.01)
(52) U.S. Cl. ........................................................ 356/479
(58) Field of Classification Search ................... 356/479
See application file for complete search history.

(56) References Cited

U.S. PATENT DOCUMENTS

| | | | |
|---|---|---|---|
| 5,956,355 A | | 9/1999 | Swanson et al. |
| 6,069,698 A * | | 5/2000 | Ozawa et al. ................. 356/511 |
| 6,134,003 A * | | 10/2000 | Tearney et al. ............... 356/479 |
| 6,564,087 B1 * | | 5/2003 | Pitris et al. .................... 600/478 |
| 7,428,052 B2 * | | 9/2008 | Fujita ............................ 356/479 |
| 2009/0039489 A1 * | | 2/2009 | Ting et al. ..................... 257/680 |
| 2009/0122320 A1 * | | 5/2009 | Petersen et al. .............. 356/477 |
| 2009/0131789 A1 * | | 5/2009 | Fehre et al. ................... 600/439 |

FOREIGN PATENT DOCUMENTS

JP    3104984 B2    9/2000

OTHER PUBLICATIONS

Jianping Su, et al., "In vivo three-dimensional microelectromechanical endoscopic swept source optical coherence tomography," Optics Express, Aug. 6, 2007, pp. 10390-10396, vol. 15, No. 16.

* cited by examiner

*Primary Examiner* — Tarifur Chowdhury
*Assistant Examiner* — Jonathon Cook
(74) *Attorney, Agent, or Firm* — Sughrue Mion, PLLC

(57) ABSTRACT

An optical tomographic image production apparatus includes an optical probe, in which a light-transmitting area that transmits measurement light and a light-blocking area that blocks the measurement light are formed. The light-blocking area is provided at a start position and an end position of the light-transmitting area. A tomographic image processing means detects an interference signal or tomographic information when the light-blocking area is irradiated with the measurement light. Further, the tomographic image processing means detects, based on the detected interference signal or tomographic information, interference signals or tomographic information obtained when the light-transmitting area is irradiated with the measurement light to produce a tomographic image in the light-transmitting area.

5 Claims, 8 Drawing Sheets

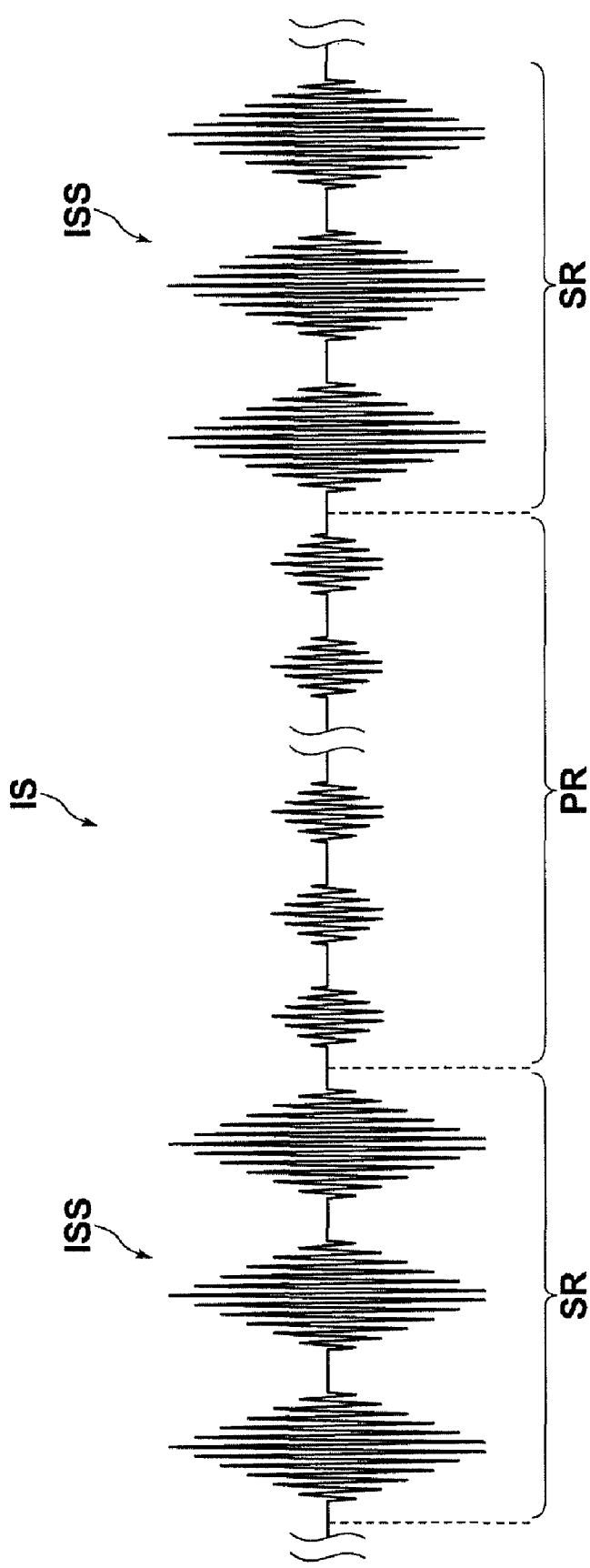

OPTICAL PROBE AND OPTICAL TOMOGRAPHIC IMAGE PRODUCTION APPARATUS USING THE PROBE

BACKGROUND OF THE INVENTION

1. Field of the Invention

The present invention relates to an optical probe that is used to produce optical tomographic images by OCT (Optical Coherence Tomography) measurement. Further, the present invention relates to a tomographic image production apparatus using the optical probe.

2. Description of the Related Art

Conventionally, when an optical tomographic image of a tissue of an organism (living body) is obtained, an optical tomographic image obtainment apparatus using OCT measurement has been used in some cases. The optical tomographic image obtainment apparatus has been used mainly to examine the fundus of eyeball (eyeground), the anterior segment of eyeball, and skin. Further, the optical tomographic image obtainment apparatus has been used in examination of various other regions of the body, such as observation of the walls of arteries using a fiber probe, and observation of digestive organs by inserting a fiber probe through a forceps channel of an endoscope. In the optical tomographic image obtainment apparatus, low coherent light output from a light source is divided into measurement light and reference light. Further, reflection light that is reflected from an object to be measured (measurement target) or backscattered light therefrom when the measurement target is irradiated with the measurement light is combined with the reference light. Then, an optical tomographic image is obtained based on the intensity of interference light of the reflection light and the reference light.

Basically, there are two types of OCT measurement, namely TD-OCT (Time Domain OCT) measurement and FD-OCT (Fourier Domain OCT) measurement. In the FD-OCT measurement, the intensity of interference light is measured for each spectral component of light without changing the optical path length of the reference light and that of the measurement light. Further, spectral analysis, such as Fourier transformation, is performed on the obtained spectral interference intensity signals by using a computer, thereby obtaining the distribution of the intensity of reflection light corresponding to the depth position of the measurement target.

When a tomographic image is obtained by the OCT measurement, it is necessary to irradiate the measurement target with measurement light in such a manner to scan the measurement target. Meanwhile, as MEMS (Micro Electro Mechanical Systems) techniques have developed in recent years, leading-end (tip) optical systems are attached to MEMS motors provided within the outer tubes of probes. Further, optical probes in which the leading-end optical systems thereof are rotationally moved by the MEMS motors with respect to axes have been disclosed (for example, please refer to Jianping Su et al., "In Vivo Three-Dimensional Microelectromechanical Endoscopic Swept Source Optical Coherence Tomography", Optics Express, vol. 15, No. 16, pp. 10390-10396, 2007). However, since it is necessary to install the MEMS motors within the probes, it is difficult to reduce the diameters of the probes. Especially, when optical probes for OCT are inserted into the body cavities of patients through forceps holes (openings) of endoscopes, since the diameters of the forceps holes are mainly 2.6 mm or 1.8 mm, it is desirable that the diameters of the optical probes are less than or equal to 1.6 mm.

Meanwhile, in the OCT measurement, a rotary joint is generally used to rotationally scan the measurement target with the measurement light (for example, please refer to Japanese Patent No. 3104984). An optical probe for OCT disclosed in Japanese Patent No. 3104984 includes a sheath that is inserted into the inside of a subject to be examined (examination subject), and a flexible shaft that extends in the longitudinal direction of the sheath within the sheath, and that can rotate with respect to the axis of the shaft. Further, the optical probe for OCT includes an optical fiber coated with the flexible shaft and a leading-end optical system that deflects light output from the optical fiber substantially at a right angle with respect to the longitudinal direction of the optical fiber. Further, the flexible shaft is rotated through a gear by a motor arranged at the base end of the optical probe, thereby rotationally moving the leading-end optical system with respect to the axis.

However, when the leading-end optical system attached to the leading end (tip) of the optical fiber is moved to rotationally scan the target by rotating the base portion of the optical fiber, as disclosed in Japanese Patent No. 3104984, there is a problem that the rotation of the leading-end optical system becomes irregular because of friction between the shaft and the probe outer-tube (outer-cylinder or sheath) or the like. Specifically, while the leading-end optical system makes one turn, the rotation speed of the leading-end optical system becomes low in a certain scan area, and becomes high in another scan area or the like. Consequently, scan lines with the measurement light become dense in a certain scan area, and the scan lines with the measurement light become thin in another scan area. Meanwhile, in processing for producing tomographic images, the tomographic images are produced by arranging, at equal intervals, a predetermined number of scan lines for each rotation of scan. Therefore, there are cases in which a position of the measurement target that is actually irradiated with measurement light differs from a position of the measurement target that is represented in the tomographic image, thereby deteriorating the image quality of the tomographic image.

SUMMARY OF THE INVENTION

In view of the foregoing circumstances, it is an object of the present invention to provide an optical probe that can prevent deterioration in the image quality of tomographic images, caused by irregular rotation of the leading-end optical system of the optical probe. Further, it is an object of the present invention to provide an optical tomographic image production apparatus using the optical probe.

An optical probe according to the present invention is an optical probe comprising:

a probe outer-tube that has substantially cylindrical form, and which is inserted into a subject to be examined;

an optical fiber that is arranged in the inner space of the probe outer-tube in the longitudinal direction thereof; and a leading-end optical system that is rotatable with respect to the probe outer-tube, and which deflects light output from the leading end of the optical fiber toward a measurement target in the subject to be examined, wherein the probe outer-tube has a light-transmitting area and a light-blocking area, and wherein the light-transmitting area is formed along a rotation direction of the optical fiber and transmits the light output from the leading-end optical system, and wherein the light-blocking area is formed at a start position and an end position of the light-transmitting area and blocks the light output from the leading-end optical system.

An optical tomographic image production apparatus according to the present invention is an optical tomographic image production apparatus comprising:

a light source unit that emits light;

a light division means that divides the light emitted from the light source unit into measurement light and reference light;

an optical probe;

a light combination means that combines reflection light and the reference light, the reflection light being reflected from the measurement target when the measurement target is irradiated with the measurement light, which has been guided by the optical probe, in such a manner to scan the measurement target;

an interference light detection means that detects, as an interference signal, interference light of the reflection light and the reference light that have been combined by the light combination means for each scan line, thereby detecting a plurality of interference signals; and a tomographic image processing means that obtains tomographic information about the measurement target by using the interference signal that has been detected by the interference light detection means for each scan line, and obtains a tomographic image of the measurement target by using the tomographic information, wherein the probe outer-tube of the optical probe has a light-transmitting area and a light-blocking area, and wherein the light-transmitting area is formed along a rotation direction of the optical fiber and transmits the light output from the leading-end optical system, and wherein the light-blocking area is formed at a start position and an end position of the light-transmitting area and blocks the light output from the leading-end optical system, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means.

Here, the reflection light is reflection light from the measurement target and backscattered light therefrom.

Further, the structure of the light-blocking area is not particularly limited as long as the light-blocking area blocks measurement light. The light-blocking area may block the measurement light by reflecting the measurement light toward the leading-end optical system side. Alternatively, the light-blocking area may block the measurement light by absorbing or scattering the measurement light.

Further, the light-blocking-area detection means may detect the light-blocking area by using the signal level of the interference signal detected, for each scan line, by the interference light detection means. Alternatively, the light-blocking-area detection means may detect the light-blocking area by using tomographic information obtained, for each scan line, by the tomographic information obtainment means.

For example, the light-blocking area may reflect the measurement light that has been output from the leading-end optical system toward the leading-end optical system side. Further, the light-blocking-area detection means may recognize the position of the light-blocking area by judging whether the signal level of each of the interference signals exceeds a predetermined threshold value. Further, the light-transmitting-area detection means may detect the light-transmitting area based on the position of the light-blocking area. Alternatively, when the light-blocking area absorbs or scatters the measurement light that has been output from the leading-end optical system, the light-blocking-area detection means may recognize the position of the light-blocking area by judging whether the signal level of each of the interference signals is lower than a predetermined threshold value. Further, the light-transmitting-area detection means may detect the light-transmitting area based on the position of the light-blocking area.

Further, when the light-blocking area reflects the measurement light that has been output from the leading-end optical system toward the leading-end optical system side, the light-blocking-area detection means may recognize the light-blocking area by judging whether the tomographic information, for each scan line, that corresponds to the position of the probe outer-tube exceeds a predetermined threshold value. Further, the light-transmitting-area detection means may detect the light-transmitting area based on the light-blocking area. Alternatively, when the light-blocking area absorbs or scatters the measurement light that has been output from the leading-end optical system, the light-blocking-area detection means may recognize the light-blocking area by judging whether the tomographic information that corresponds to the position of the probe outer-tube is lower than a predetermined threshold value. Further, the light-transmitting-area detection means may detect the light-transmitting area based on the light-blocking area.

Further, the tomographic image production means may include a scan line judgment means that judges whether the number of scan lines constituting the light-transmitting area is a set scan line number. When the scan line judgment means judges that the number of the scan lines exceeds the set scan line number, the tomographic image production means may correct the image quality to reduce the number of the scan lines so that the number of the scan lines constituting the light-transmitting area becomes the set scan line number. Further, when the scan line judgment means judges that the number of the scan lines is smaller than the set scan line number, the tomographic image production means may correct the image quality to increase the number of the scan lines so that the number of the scan lines constituting the light-transmitting area becomes the set scan line number.

The optical tomographic image production apparatus may obtain the tomographic images by so-called FD-OCT measurement. Alternatively, the optical tomographic image production apparatus may obtain the tomographic images by so-called TD-OCT measurement.

The optical tomographic image production apparatus using the optical probe according to the present invention is an optical tomographic image production apparatus comprising:

a light source unit that emits light;

a light division means that divides the light emitted from the light source unit into measurement light and reference light;

an optical probe;

a light combination means that combines reflection light and the reference light, the reflection light being reflected from the measurement target when the measurement target is irradiated with the measurement light, which has been guided by the optical probe, in such a manner to scan the measurement target;

an interference light detection means that detects, as an interference signal, interference light of the reflection light and the reference light that have been combined by the light combination means for each scan line, thereby detecting a plurality of interference signals; and a tomographic image processing means that obtains tomographic information about the measurement target by using the interference signal that has been detected by the interference light detection means for each scan line, and obtains a tomographic image of the measurement target by using the tomographic information, wherein the probe outer-tube of the optical probe has a light-transmitting area and a light-blocking area, and wherein the light-transmitting area is formed along a rotation direction of the optical fiber and transmits the light output from the leading-end optical system, and wherein the light-blocking area is formed at a start position and an end position of the light-transmitting area and blocks the light output from the leading-end optical system, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means. Therefore, the optical tomographic image production apparatus according to the present invention produces the tomographic image in the light-transmitting area by identifying the interference signal or the tomographic information obtained in the light-transmitting area in the plurality of interference signals or the plurality of pieces of tomographic information, which are obtained for each scan line, respectively. Therefore, even if the rotation is irregular, it is possible to produce the tomographic image of the light-transmitting area by using the interference signal obtained when the light-transmitting area is irradiated with the measurement light. Hence, it is possible to prevent deterioration in the image quality of the tomographic image due to irregular rotation of the leading-end optical system.

Further, when the light-blocking area reflects the measurement light that has been output from the leading-end optical system toward the leading-end optical system side, and the light-blocking-area detection means detects the light-blocking area by judging whether the signal level of each of the interference signals exceeds a predetermined threshold value, the light-transmitting area can be detected without performing spectral analysis on the interference signals. Therefore, it is possible to perform efficient tomographic image processing.

Further, when the light-blocking area absorbs or scatters the measurement light that has been output from the leading-end optical system, and the light-blocking-area detection means detects the light-blocking area by judging whether the signal level of each of the interference signals is lower than a predetermined threshold value, the light-transmitting area can be detected without performing spectral analysis on the interference signals. Therefore, it is possible to perform efficient tomographic image processing.

Further, when the light-blocking area reflects the measurement light that has been output from the leading-end optical system toward the leading-end optical system side, and the light-blocking-area detection means detects the light-blocking area by judging whether the tomographic information that corresponds to the position of the probe outer-tube exceeds a predetermined threshold value, it is possible to accurately detect the light-transmitting area.

Further, when the light-blocking area absorbs or scatters the measurement light that has been output from the leading-end optical system, and the light-blocking-area detection means detects the light-blocking area by judging whether the tomographic information that corresponds to the position of the probe outer-tube is lower than a predetermined threshold value, it is possible to accurately detect the light-transmitting area.

Further, the tomographic image production means thins scan lines constituting the light-transmitting area detected by the light-transmitting-area detection means so that the number of the scan lines becomes a set number when the number of the scan lines exceeds the set number. The tomographic image production means interpolates a scan line or scan lines in the light-transmitting area so that the number of the scan lines becomes the set number when the number of the scan lines is smaller than the set number. If the tomographic image production means thins the scan lines or interpolates the scan line as described above, when the tomographic image in the light-transmitting area is displayed as a motion image (dynamic image or video image) by repeating scanning with the measurement light, it is possible to display the motion image in such a manner that consecutive image frames of the motion image have substantially the same image quality.

BRIEF DESCRIPTION OF THE DRAWINGS

FIG. 7 is a schematic diagram illustrating an example of interference signals obtained, for each scan line, by an interference signal obtainment means illustrated in FIG. 6;

DESCRIPTION OF THE PREFERRED EMBODIMENTS

Figure 1:
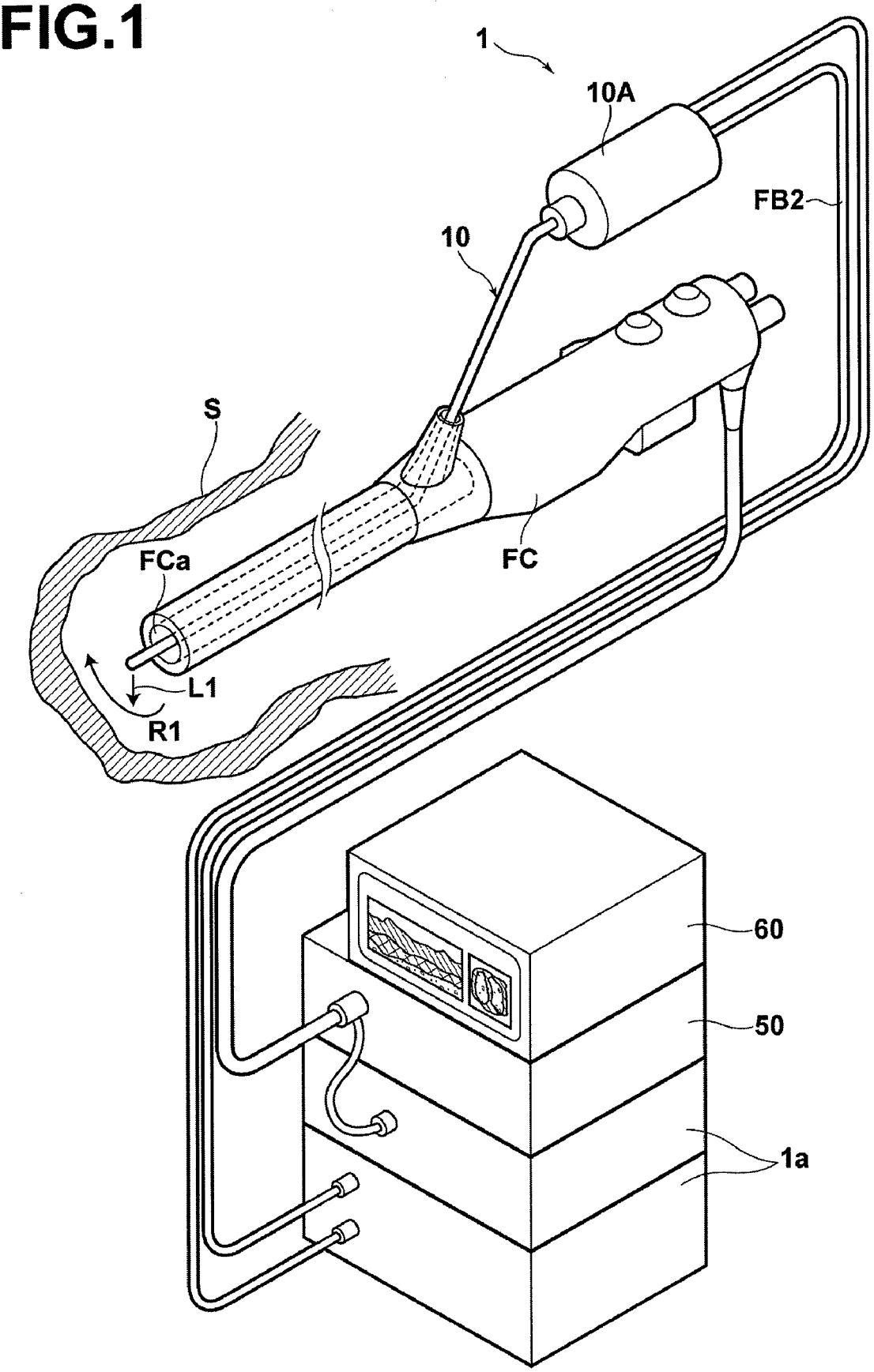
FIG. 1 is a schematic diagram illustrating the configuration of an embodiment of an optical tomographic image production apparatus according to the present invention.

Hereinafter, embodiments of an optical tomographic image production apparatus according to the present invention will be described with reference to drawings. FIG. 1 is a schematic diagram illustrating the configuration of an embodiment of an optical tomographic image production apparatus according to the present invention. An optical tomographic image production apparatus 1 obtains tomographic image P of object S to be measured (measurement target S), such as organism tissue and cells in the body cavity of a patient (in vivo), by inserting an optical probe 10 into the body cavity of the patient by using forceps hole FC of an endoscope and by projecting the optical probe 10 from forceps channel FCa of the endoscope. The optical probe 10 is optically connected to an interferometer 1a by optical fiber FB2.

Figure 2:
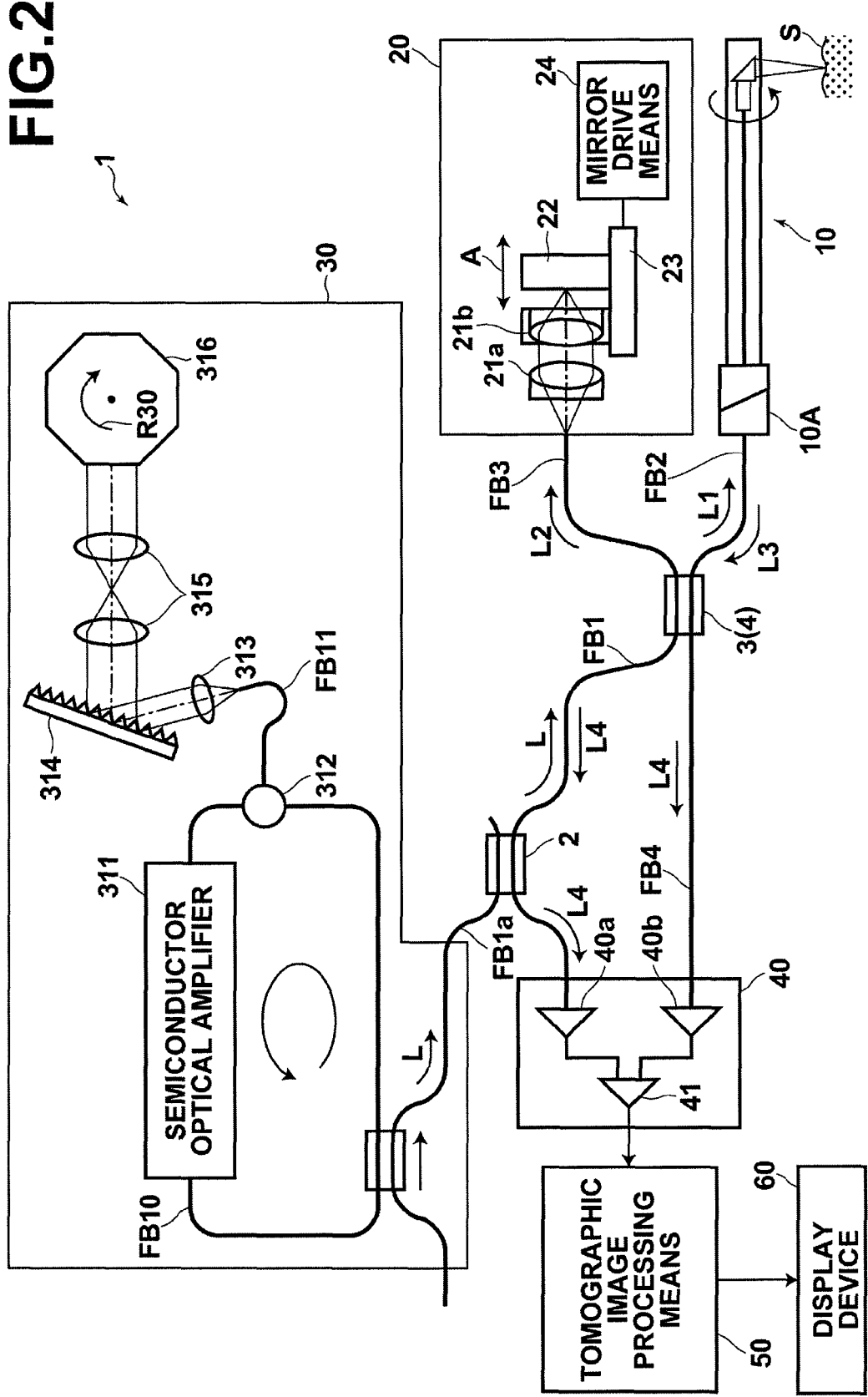
FIG. 2 is a schematic diagram illustrating an embodiment of the optical tomographic image production apparatus.

FIG. 2 is a schematic diagram illustrating the configuration of the optical tomographic image production apparatus 1 illustrated in FIG. 1. The optical tomographic image production apparatus 1 obtains a tomographic image of the measurement target S by SS-OCT (Swept Source OCT) measurement. The optical tomographic image production apparatus 1 includes a light source unit 30, a light division means 3, a light combination means 4, an interference light detection means 40, a tomographic image processing means 50, and the like.

The light source unit 30 emits laser light L in such a manner to sweep the wavelength of light at constant cycles To. Specifically, the light source unit 30 includes a semiconductor optical amplifier (semiconductor gain medium) 311 and optical fiber FB10, and the optical fiber FB10 is connected to both ends of the semiconductor optical amplifier 311. The semiconductor optical amplifier 311 outputs very weak light toward an end of the optical fiber FB10 when drive electric current is injected into the semiconductor optical amplifier 311. Further, the semiconductor optical amplifier 311 amplifies light input thereto from the other end of the optical fiber FB10. When drive current is supplied to the semiconductor optical amplifier 311, laser light L is output to the optical fiber FB10 by an optical resonator that is formed by the semiconductor optical amplifier 311 and the optical fiber FB10.

Further, an optical splitter 312 is connected to the optical fiber FB10. Therefore, a part of light that propagates through the optical fiber FB10 is output to optical fiber FB11 side from the optical splitter 312. The light output from the optical fiber FB11 is transmitted through a collimator lens 313, a diffraction grating device 314, and an optical system 315, and reflected by a rotary polygon mirror 316. Further, the reflected light is transmitted through the optical system 315, the diffraction grating device 314, and the collimator lens 313, and reenters the optical fiber FB11.

Here, the rotary polygon mirror 316 rotates in the direction of arrow R30, and the angle of each reflection plane of the rotary polygon mirror 316 changes with respect to the optical axis of the optical system 315. Accordingly, light only in a specific wavelength band of the light that has been divided by the diffraction grating device 314 returns to the optical fiber FB11. The wavelength of the light that returns to the optical fiber FB11 is determined by the angle formed by the optical axis of the optical system 315 and the reflection plane. Further, the light having the specific wavelength that has entered the optical fiber FB11 enters the optical fiber FB10 through the optical splitter 312. Further, laser light L that has a specific wavelength is output to the optical fiber FB1a side.

Figure 3:
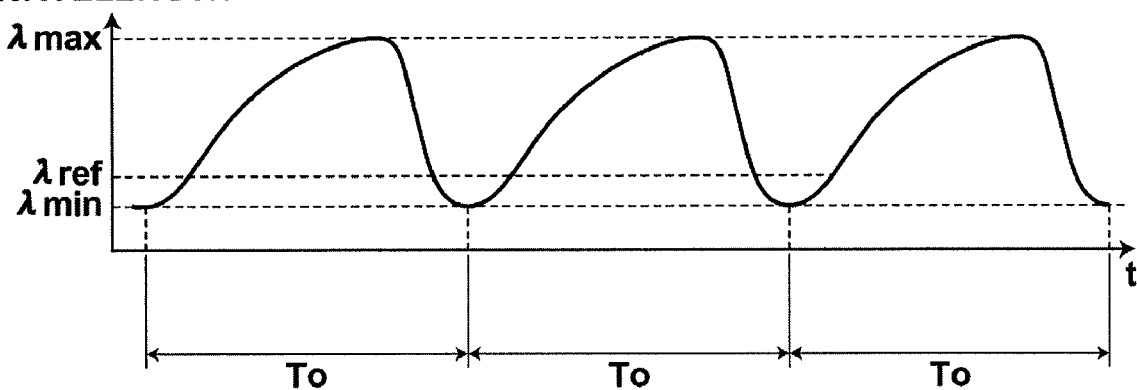
FIG. 3 is a graph showing wavelength sweeping of light output from a light source unit illustrated in FIG. 2.

Therefore, when the rotary polygon mirror 316 rotates at constant speed in the direction of arrow R30, the wavelength $\lambda$ of light that enters the optical fiber FB1a cyclically changes according to time. Specifically, as illustrated in FIG. 3, the light source unit 30 outputs light L, the wavelength of which is swept at constant cycles To (for example, approximately 50 μsec) from the minimum sweep wavelength $\lambda$min to the maximum wavelength $\lambda$max.

In the above description, a light source 30 in which the wavelength is swept by rotation of the polygon mirror has been used as an example. The light may be output while the wavelength of the light is cyclically swept by using a known technique, such as an ASE (amplified spontaneous emission) optical light source unit.

The light division means 3 is a 2×2 optical fiber coupler, for example. The light division means 3 divides the light L that has been output from the light source unit 30 and propagated through the optical fiber FB1 into measurement light L1 and reference light L2. At this time, the light division means 3 divides the light at the ratio of measurement light L1:reference light L2=99:1, for example. The light division means 3 is optically connected two optical fibers, namely optical fibers FB2 and FB3. The measurement light L1, which has been obtained by division, is input to the optical fiber FB2 side, and the reference light L2, which has been obtained by division, is input to the optical fiber FB3 side.

Figure 4:
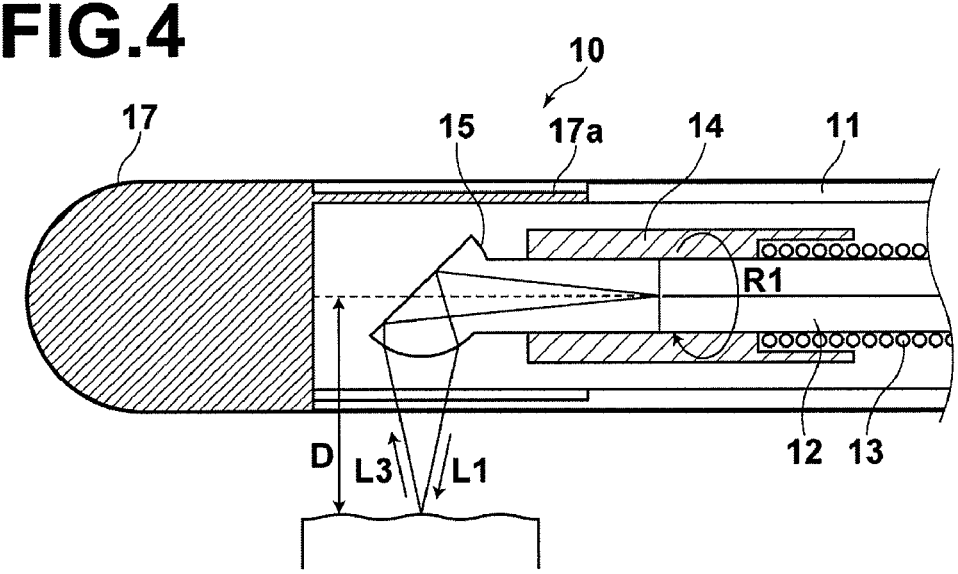
FIG. 4 is a schematic diagram illustrating an example of an optical probe used in the optical tomographic image production apparatus illustrated in FIG. 2.
Figure 5:
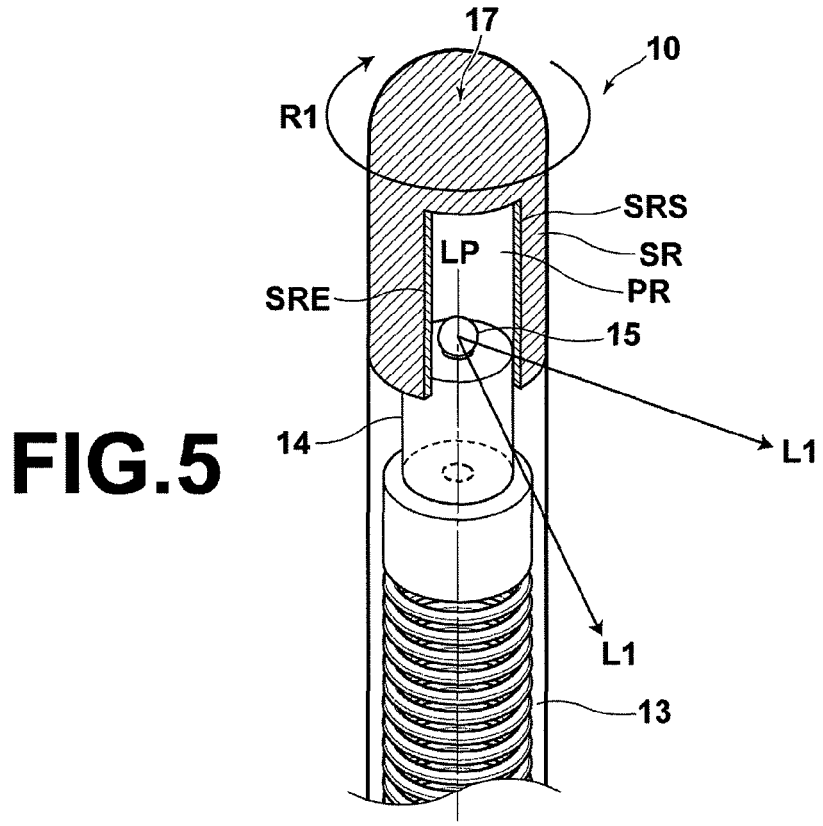
FIG. 5 is a schematic diagram illustrating an example of an optical probe used in the optical tomographic image production apparatus illustrated in FIG. 2.

Further, the optical fiber FB2 is optically connected to the optical probe 10, and the measurement light L1 propagates through the optical probe 10. FIG. 4 is a diagram illustrating a cross section of the leading-end portion of the optical probe 10 according to an embodiment of the present invention. FIG. 5 is a schematic perspective view of the leading-end portion of the optical probe 10. The optical probe 10 includes a probe outer-tube 11, an optical fiber 12, a flexible shaft 13, and a leading-end optical system 15. The probe outer-tube 11 is formed by a flexible member having cylindrical form. Further, the leading end of the probe outer-tube 11 is sealed (closed) by a cap 17.

The optical fiber 12 is arranged in the inner space of the probe outer-tube 11 in the longitudinal direction thereof. The optical fiber 12 guides the measurement light L1 to the measurement target S. Further, the optical fiber 12 guides the reflection light L3 from the measurement target S when the measurement light S is irradiated with the measurement light L1. The flexible shaft 13 is fixed onto the outer circumference of the optical fiber 12. The flexible shaft 13 is formed by a dense coil, which is a metal wire member wound around the outer circumference of the optical fiber 12. Further, the optical fiber 12 is rotated by rotation of the flexible shaft 13 in the direction of arrow R1.

The leading-end optical system 15 deflects the light output from the leading end of the optical fiber 12 toward the measurement target S. The leading-end optical system 15 has a condensing lens that has substantially spherical form. The leading-end optical system 15 deflects the measurement light L1 output from the optical fiber 12 toward the measurement target S side, and condenses the measurement light L1 onto the measurement target S. Further, the leading-end optical system 15 causes the reflection light L3, reflected from the measurement target S when the measurement target S is irradiated with the measurement light L1, to enter the optical fiber 12. For example, the focal length of the leading-end optical system 15 is approximately at distance D=3 mm in the direction of the diameter of the probe outer-tube 11 from optical axis LP of the optical fiber 12.

The leading-end optical system 15 is fixed onto the optical fiber 12 by a fixing member 14, and rotates in the direction of arrow R1 together with the optical fiber 12. Therefore, the measurement target S is irradiated with the measurement light L1, which is output from the leading-end optical system 15, in such a manner to scan the measurement target S in the direction of arrow R1.

Here, the probe outer-tube 11 includes a light-transmitting area PR and a light-blocking area SR formed therein. The light-transmitting area PR transmits the measurement light L1 output from the leading-end optical system 15, and the light-blocking area SR blocks the measurement light L1 output from the leading-end optical system 15. The light-transmitting area PR is formed along the rotation direction of the leading-end optical system 15. The light-blocking area SR is formed at a start position and an end position of the light-transmitting area PR. The light-transmitting area PR and the light-blocking area SR are formed, by the cap 17, on the inner-wall-side of the probe outer-tube 11.

Specifically, an insertion portion 17a of the cap 17, the insertion portion 17a inserted into the probe outer-tube 11, has cylindrical form, and a cut (a cut portion or a notch) is formed in a portion of the side-wall surface of the insertion portion 17a. When the cap 17 is inserted into the probe outer-tube 11, the cut portion forms the light-transmitting area PR, and the insertion portion 17a other than the cut portion forms the light-blocking area SR. Therefore, in FIGS. 3 and 4, only one light-transmitting area PR that has fan shape (sector shape) having a central angle within the range of 30° to 90° is formed with respect to the diameter direction of the measurement light L1 (the direction of arrow R1). In the other area, the light-blocking area SR is formed. Further, at the boundaries between the light-blocking area SR and the light-transmitting area PR, a start light-blocking area SRS and an end light-blocking area SRE are formed. The start light-blocking area SRS is a start position of the light-transmitting area PR, and the end light-blocking area SRE is an end position of the light-transmitting area PR.

Here, the light-blocking area SR is made of a reflector, and reflects the measurement light L1 that has been output from the leading-end optical system 15 toward the leading-end optical system side. The light-blocking area SR is formed, for example, by depositing a reflection coating onto the inner wall of the insertion portion 17a of the cap 17, or by attaching a reflection tape thereto. Therefore, in the light-blocking area SR, the measurement light L1 is not output to the measurement target S on the outside of the probe outer-tube 11.

In the above description, a case in which the light-blocking area SR reflects light has been described. Alternatively, the light-blocking area SR may absorb (or scatter) light. Further, a case in which the light-transmitting area PR and the light-blocking area SR are formed by the cap 17 has been described. Alternatively, the light-transmitting area PR and the light-blocking area SR may be formed by attaching a tape or the like onto the inner wall surface or the outer wall surface of the probe outer-tube 11.

Meanwhile, in FIG. 2, an optical path length adjustment means 20 is provided on the reference-light-L2 output side of the optical fiber FB3. The optical path length adjustment means 20 changes the optical path length of the reference light L2 to adjust the position of starting obtainment of a tomographic image. The optical path length adjustment means 20 includes a reflection mirror 22, a first optical lens 21a and a second optical lens 21b. The reflection mirror 22 reflects the reference light L2 output from the optical fiber FB3, and the first optical lens 21a and the second optical lens 21b are arranged between the reflection mirror 22 and the optical fiber FB3. The reference light L2 that has been output from the optical fiber FB3 is collimated by the first optical lens 21a, and condensed onto the reflection mirror 22 by the second optical lens 21b. Then, the reference light L2 is reflected by the reflection mirror 22. Further, the reflected light is collimated by the second optical system 21b, and condensed onto the optical fiber FB3 by the first optical lens 21a.

Further, the optical path length adjustment means 20 includes a base 23 and a mirror movement means 24. The second optical lens 21b and the reflection mirror 22 are fixed onto the base 23, and the mirror movement means 24 moves the base 23 in the direction of the optical axis of the first optical lens 21a. The optical path length of the reference light L2 is changed by moving the base 23 in the direction of arrow A.

The light combination means 4 is a 2×2 optical fiber coupler, as described above. The light combination means 4 combines the reference light L2, the optical path length of which has been changed by the optical path length adjustment means 20, and the reflection light L3, reflected from the measurement target S. Further, the light combination means 4 splits the interference light L4 into the optical fibers FB1 and FB4 to output the interference light L4 toward the interference detection means 40 side.

The interference light detection means 40 detects, as an interference signal IS, the interference light L4 of the reflection light L3 and the reference light L2, which have been combined by the light combination means 4. The interference light detection means 40 includes two light detection units (detectors) 40a and 40b and a differential amplifier 41. Each of the light detectors 40a and 40b detects the interference light L4 that has propagated through the optical fibers FB1 and FB4, respectively. Further, an output from each of the light detectors 40a and 40b is input to the differential amplifier 41. The differential amplifier 41 outputs, as an interference signal IS, a difference between the interference light output from the light detector 40a and the interference light output from the light detector 40b. Since balanced detection of two beams of interference light L4 is performed by the differential amplifier 41 as described above, it is possible to remove common-mode optical noise, other than the interference signal IS, while amplifying the interference signal IS. Hence, the image quality of the tomographic image P is improved.

Figure 6:
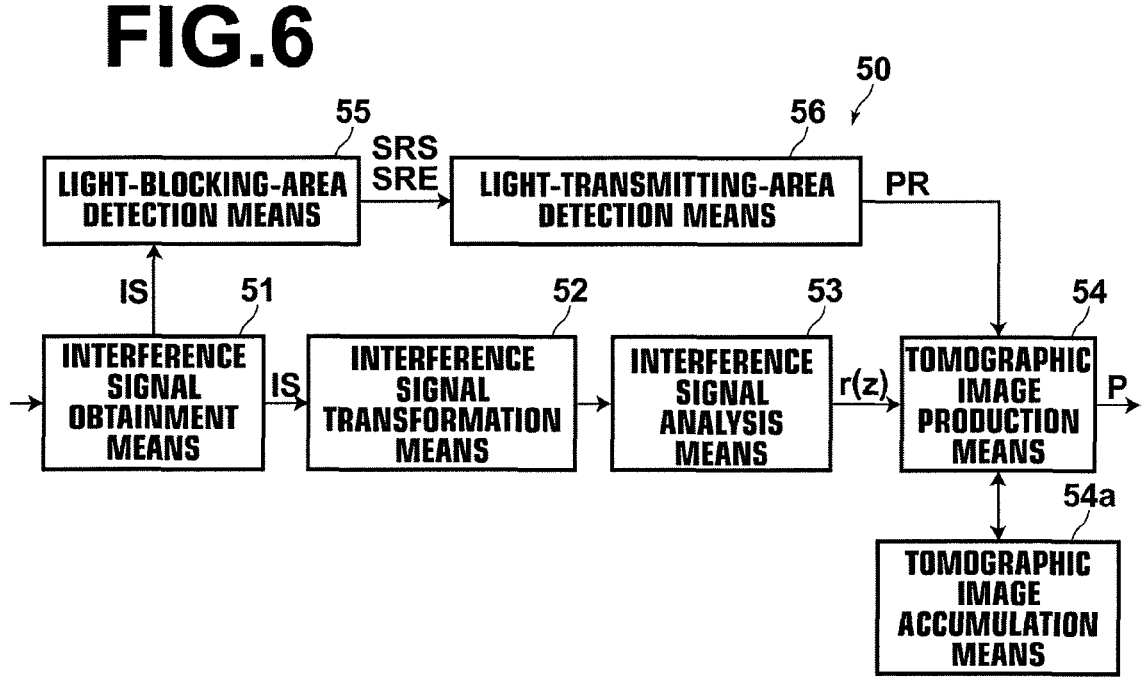
FIG. 6 is a block diagram illustrating an example of a tomographic image processing means illustrated in FIG. 2.

FIG. 6 is a block diagram illustrating an example of the tomographic image processing means 50 illustrated in FIG. 1. The configuration of the tomographic image processing means 50 is realized by causing a computer (for example, a personal computer or the like) to execute a tomographic image processing program installed in an auxiliary storage device (a supplementary storage device). The tomographic image processing means 50 includes an interference signal obtainment means 51, an interference signal transformation means 52, an interference signal analysis means 53, a tomographic image production means 54, a light-blocking-area detection means 55, a light-transmitting-area detection means 56 and the like.

As illustrated in FIG. 7, the interference signal obtainment means 51 obtains the interference signal IS detected by the interference light detection means 40 for each scan line. Specifically, the interference light detection means 40 detects an interference signal IS for one scan line each time when the light source unit 30 sweeps wavelengths for one cycle. Further, the interference signal obtainment means 51 obtains the interference signal IS for each scan line, the interference signal IS having been detected by the interference light detection means 40 for each scan line.

Figure 8A:
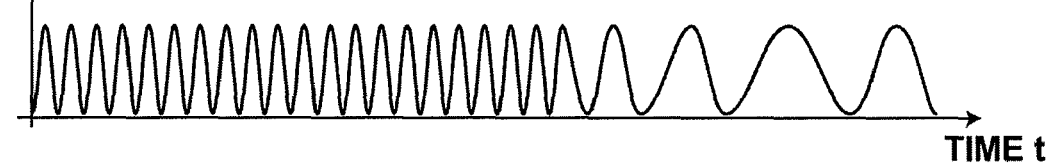
FIG. 8A is a graph showing interference signals obtained by an interference signal obtainment means illustrated in FIG. 6.
Figure 8B:
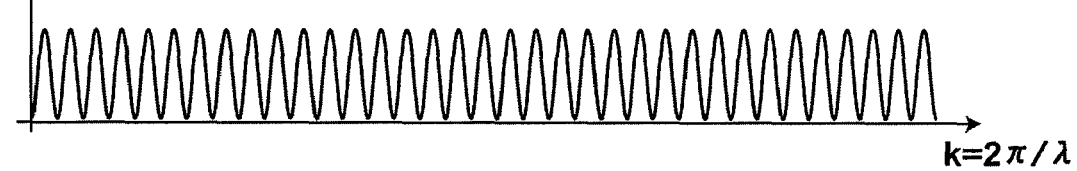
FIG. 8B is a graph showing an example of re-sampled interference signals.

The interference signal transformation means 52 has a function for re-arranging, as illustrated in FIG. 8B, the interference signals IS that are arranged as illustrated in FIG. 8A. FIG. 8A illustrates the interference signals IS detected as the signal levels that change according to time. In FIG. 8B, the interference signals IS are re-arranged at equal intervals with respect to the axis of the wave number k ($=2\pi/\lambda$). Specifically, the interference signal transformation means 52 maintains a time-wavelength sweep characteristic data table or function of the light source unit 30 in advance. The interference signal transformation means 52 re-arranges the interference signals IS at equal intervals with respect to the axis of the wave number k by using the time-wavelength sweep characteristic data table or the like. Accordingly, when tomographic information is calculated based on the interference signals IS, it is possible to use a spectral analysis method, such as a Fourier transformation processing method and a maximum entropy method, which require that the signals to be analyzed are arranged at equal intervals in frequency space. Therefore, it is possible to obtain highly accurate tomographic information. This signal transformation method is disclosed in the specification of U.S. Pat. No. 5,956,355 in detail.

The interference signal analysis means 53, illustrated in FIG. 6, analyzes the interference signals IS on which signal transformation has been performed by the interference signal transformation means 52. The analysis is performed by using a known spectral analysis technique, such as a Fourier transformation processing method, a maximum entropy method (MEM), and a Yule-Walker method. Consequently, the interference signal analysis means 53 obtains tomographic information r(z) (reflectance) with respect to the depth position of the measurement target S.

The tomographic image production means 54 produces a tomographic image P based on the tomographic information r(z) that has been analyzed by the interference signal analysis means 53. Especially when the tomographic image P within the range of the light-transmitting area PR is produced, the tomographic image production means 54, which stores information about the range of the light-transmitting area PR formed at the leading end of the optical probe 10 in advance, uses the detection result obtained by the light-blocking-area detection means 55 and the light-transmitting-area detection means 56. The tomographic image production means 54 identifies, based on the detection result, the interference signals IS or the tomographic information r(z) obtained in the light-transmitting area PR to produce the tomographic image P.

The light-blocking-area detection means 55 detects a light-blocking interference signal ISS obtained in the light-blocking area SR in a plurality of interference signals IS. Specifically, the light-blocking-area detection means 55 detects the light-blocking area that is provided at the start position SRS of the light-transmitting area PR and the end position SRE of the light-transmitting area PR (please refer to FIGS. 4 and 5).

Here, when the light-blocking area blocks light by reflecting the light, the measurement light L1 is reflected in the light-blocking area SR provided in the probe outer-tube 11. Further, the reflection light L3, reflected in the light-blocking area SR, and reference light L2 are combined to produce the interference light L4. At this time, the intensity of the reflection light L3, which is reflected in the light-blocking area SR, is greatly higher than the light amount of the reflection light L3 that is reflected from the measurement target S.

Figure 9:
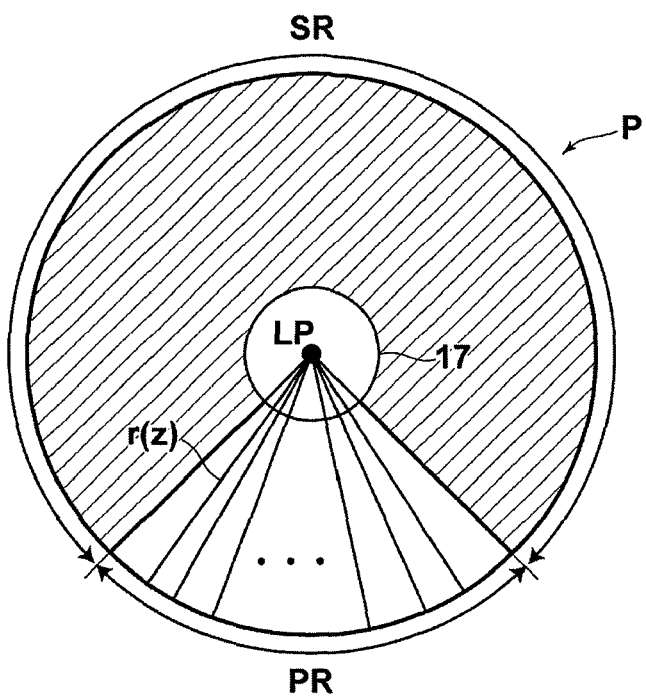
FIG. 9 is a schematic diagram illustrating an example of a tomographic image produced by a tomographic image production means illustrated in FIG. 6.

Meanwhile, the intensity of the interference light L4 depends on the intensity of the reflection light L3 and that of the reference light L2. Therefore, as the intensity of the reflection light L3 becomes higher, the signal level of the interference signal IS becomes higher. Hence, the signal level of the interference signal IS obtained in the light-blocking area SR is greatly higher than that of the interference signal obtained, for each scan line, in the light-transmitting area PR, as illustrated in FIG. 7. Therefore, the light-blocking-area detection means 55 detects the light-blocking interference signal ISS, which is obtained in the light-blocking area SR, by judging whether the signal level of the interference signal IS is higher than a predetermined threshold value. The light-transmitting-area detection means 56 identifies the start position SRS of the light-transmitting area PR and the end position SRE of the light-transmitting area PR by using the light-blocking interference signal IS detected by the light-blocking area detection means 55. Further, the light-transmitting-area detection means 56 detects the interference signals IS obtained in the light-transmitting area PR. Further, the tomographic image production means 54 produces the tomographic image P, as illustrated in FIG. 9, by using the interference signals IS in the light-transmitting area PR.

The tomographic image production means 54 may produce the tomographic image P of the light-transmitting area, based on detection result by the light-transmitting-area detection means 56, after the tomographic information r(z) is obtained by performing spectral analysis on all of the interference signals IS. Alternatively, the tomographic image production means 54 may produce the tomographic image P by performing spectral analysis only on the interference signals IS in the light-transmitting area PR detected by the light-transmitting-area detection means 56, thereby increasing the speed of processing for analysis.

Further, a case in which the light-blocking area blocks the measurement light L1 by reflecting the measurement light L1 has been described as an example. However, it is not necessary that the measurement light L1 is reflected. The light-blocking area SR can be detected based on the interference signals IS even when the light-blocking area SR blocks the measurement light L1 by absorbing the measurement light L1. Specifically, when the measurement light L1 is absorbed in the light-blocking area SR, the level of the interference signal IS in the light-blocking area SR becomes substantially the same as the light intensity level of the reference light L2, which is lower than the level of the interference signal IS in the light-transmitting area PR. Therefore, when the level of the interference signal IS is lower than a predetermined threshold value, the light-blocking-area detection means 55 may recognize that the interference signal IS is a signal in the light-blocking area SR.

Further, the tomographic image production means 54 has a function for performing image-quality enhancement processing based on the number of scan lines forming the light-transmitting area detected by the light-transmitting-area detection means 56. Specifically, when the scan speed with the measurement light L1 (the rotation speed of the leading-end optical system 15) in the light-transmitting area PR is low, the number of scan lines in the light-transmitting area PR becomes smaller than a set scan line number. At this time, the tomographic image production means 54 interpolates a scan line or scan lines to produce a tomographic image constituted of scan lines in the set number. The tomographic image production means 54 may interpolate the scan lines, for example, by using a known technique, such as spline interpolation.

When the scan speed with the measurement light L1 (the rotation speed of the leading-end optical system 15) in the light-transmitting area PR is high, the number of scan lines in the light-transmitting area PR becomes larger than the set scan line number. At this time, the tomographic image production means 54 thins (reduces) the scan lines to produce a tomographic image P constituted of scan line in the set number. The tomographic image production means 54 reduces the scan lines, for example, by using a known technique, such as a method of deleting scan lines or a method of producing a tomographic image by using an average value of tomographic information r(z) for a plurality of scan lines.

Next, with reference to FIGS. 1 through 9, an example of the operation of the optical tomographic image production apparatus 1 will be described. First, light L, the wavelength of which is swept, is output from the light source unit 30 (please refer to FIG. 3). The light division means 3 divides the light L into measurement light L1 and the reference light L2. The measurement light L1 propagates through the optical fiber FB2 and the inside of the optical probe 10. Further, the measurement light 11 is output from the optical probe 10 to irradiate the measurement target S in such a manner to rotationally scan the measurement target S. Then, reflection light L3 that is reflected from the measurement target S when the measurement target S is irradiated with the measurement light L1 is input to the light combination means 4 through the optical probe 10. Meanwhile, the reference light L2 is input to the optical path length adjustment means 20 through the optical fiber FB3, and collimated by the first optical lens 21*a*. Further, the collimated light is condensed onto the reflection mirror 22 by the second optical lens 21*b*, and reflected by the reflection mirror 22. The reflected reference light L2 is collimated by the second optical lens 21*b*, and caused to enter the optical fiber FB3 by the first optical lens 21*a*. At this time, the distance between the first optical lens 21*a* and the second optical lens 21*b* is adjusted by the mirror drive means 24 to adjust the optical path length of the reference light L2. Further, the reference light L2 propagates through the optical fiber FB3, and enters the light combination means 4.

The light combination means 4 combines the reflection light L3 and the reference light L2. Further, the interference light L4 of the reflection light L3 and the reference light L2 is split and input to each of the optical fibers FB1 and FB4. After then, the interference light detection means 40 performs balanced detection on the split interference light L4, and obtains the interference signal IS.

Then, in the tomographic image processing means 50, illustrated in FIG. 6, the interference signal obtainment means 51 obtains the interference signal IS for each scan line. Further, the interference signal transformation means 52 transforms the interference signal IS into the intensity of signal with respect to the wave number. Further, the interference signal analysis means 53 performs spectral analysis on the interference signal IS to obtain the tomographic information r(z) about the measurement target S.

Meanwhile, the light-blocking-area detection means 55 detects the light-blocking interference signal ISS, which has been obtained in the light-blocking area SR, in the plurality of interference signals IS, which have been obtained for each scan line. Further, the light-transmitting-area detection means 56 detects, as the interference signals in the light-transmitting area PR, the interference signals IS that have been obtained in the period between the light-blocking interference signals ISS.

After then, the tomographic image production means 54 produces the tomographic image P by using the tomographic information r(z) obtained, by the interference signal analysis means 53, by performing spectral analysis on the interference signals IS in the light-transmitting area PR (please refer to FIG. 9). At this time, when the number of lines (line number) of the interference signal IS in the light-transmitting area PR is larger than a set line number, the tomographic image production means 54 performs processing to reduce the line number (thinning). When the number of lines (line number) of the interference signal IS in the light-transmitting area PR is smaller than the set line number, the tomographic image production means 54 performs processing to interpolate lines to increase the line number (interpolation).

As described above, the tomographic image P in the light-transmitting area PR is produced by detecting the interference signals IS obtained in the light-transmitting area PR. Therefore, even if the rotational scan speed becomes irregular, it is possible to prevent deterioration in the image quality of the tomographic image. Specifically, in production of the tomographic image, as described above, when the leading-end optical system 15 is rotationally moving at constant speed, the intervals of the scan lines are substantially uniform through the entire scan area. Therefore, the light-transmitting area PR is formed based on the tomographic information r(z) (interference signal IS) for the set scan line number. However, when the optical probe 10 is actually bent and inserted into the body cavity of a patient, the probe outer-tube 11 and the flexible shaft 13 contact with each other, and the rotation becomes irregular in some cases. In such a case, the intervals of the scan lines with the measurement light L1 become irregular through the entire scan area. Even in such a case, in which the intervals of the scan lines are irregular, the tomographic image production means 54 produces the tomographic image P by arranging the scan lines at equal intervals, thereby deteriorating the image quality of the tomographic image P.

In contrast, the interference signal IS that is obtained when the light-transmitting area PR is irradiated with the measurement light L1 maybe detected by detecting the light-blocking interference signal ISS obtained in the light-blocking area. Further, the tomographic image P of the light-transmitting area PR may be produced by using the detected interference signal. If processing is performed in such a manner, it is possible to prevent a shift in position between the irradiation position with the measurement light L1 and the display position of the tomographic image P, the shift being caused by the irregular rotation. Hence, it is possible to prevent deterioration in the image quality.

Further, even when an encoder is provided in a rotary joint portion 10A of the optical fiber 12, and the rotary joint portion 10A can detect the irradiation position with the measurement light L1, the phase of the rotation of the optical fiber 12 and that of the rotation of the leading-end optical system 15 may be shifted from each other due to twisting of the optical fiber 12, the flexible shaft 13 or the like in some cases. Further, the detection result of the irradiation position with the measurement light L1 by the rotary encoder may be shifted from the actual irradiation position by the leading-end optical system 15. In such a case, when the optical probe 10 as illustrated in FIG. 2 is used, it is possible to accurately detect the rotation of the leading-end optical system 15, because the irradiation with the measurement light L1 is detected by identifying the light-blocking area SR formed at the leading end of the probe outer-tube 11.

Figure 10:
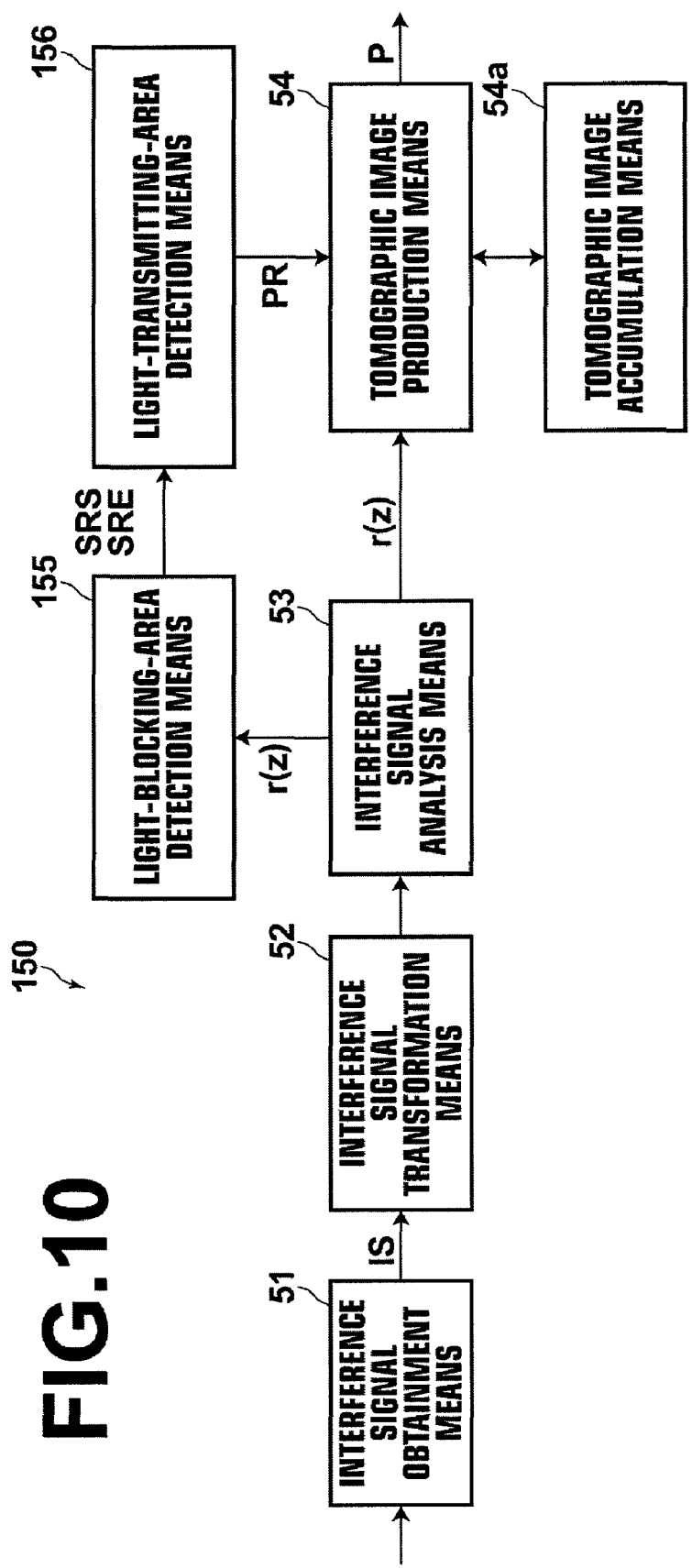
FIG. 10 is a block diagram illustrating another embodiment of the tomographic image processing means in the tomographic image production apparatus illustrated in FIG. 2.

FIG. 10 is a block diagram illustrating another embodiment of the tomographic image processing means in the tomographic image production apparatus of the present invention. A tomographic image processing means 150 will be described with reference to FIG. 10. In the tomographic image processing means 150, illustrated in FIG. 10, the same reference numerals will be assigned to elements corresponding to the elements in the tomographic image processing means 50 illustrated in FIG. 6, and the explanation thereof will be omitted. The tomographic image processing means 150, illustrated in FIG. 10, differs from the tomographic image processing means 50, illustrated in FIG. 6, in that the tomographic image processing means 150 detects the light-blocking area SR by using the tomographic information r(z) after spectral analysis.

A light-blocking-area detection means 155 detects the light-blocking area SR based on the tomographic information r(z) obtained for each scan line. Here, distance zh from the light output portion of the leading-end optical system 15 to the light-blocking area SR is known. Therefore, the light-blocking area SR is detected by using the tomographic information r(zh) obtained by spectral analysis. At this time, when the light-blocking area SR is formed by a reflecting member (reflective substance), judgment is made as to whether the signal level of the tomographic information r(zh) is higher than or equal to a predetermined threshold value to detect the light-blocking area SR. When the light-blocking area SR absorbs light, judgment is made as to whether the signal level of the tomographic information r(zh) is less than or equal to a predetermined threshold value to detect the light-blocking area SR. Further, the light-transmitting area detection means 156 detects, as the tomographic information r(z) obtained in the light-transmitting area PR, the tomographic information r(z) for each scan line between the periods of the light-blocking tomographic information rs(z) detected by the light-blocking area detection means 155.

In this case, the tomographic image P of the light-transmitting area PR is produced by using the tomographic information r(z) obtained when the light-transmitting area PR is actually irradiated with the measurement light L1, it is possible to prevent deterioration in the image quality due to irregular rotation. Further, it is possible to accurately detect the light-blocking area SR based on the tomographic information r(z) after spectral analysis.

According to the aforementioned embodiments, the optical tomographic image production apparatus includes the light source unit 30, the light division means 3, the optical probe 10, the light combination means 4, the interference light detection means 40, and the tomographic image processing means 50. The light source unit 30 outputs light, and the light division means 3 divides the light output from the light source unit into measurement light L1 and reference light L2. The optical probe 10 guides the measurement light L1 to measurement target S, and the light combination means 4 combines reflection light L3 and the reference light L2, the reflection light being reflected from the measurement target S when the measurement target S is irradiated with the measurement light L1, which has been guided by the optical probe 10, in such a manner to scan the measurement target S. The interference light detection means 40 detects, as an interference signal IS, interference light of the reflection light L3 and the reference light L2 that have been combined by the light combination means for each scan line, thereby detecting a plurality of interference signals. The tomographic image processing means 50 obtains tomographic information r(z) about the measurement target S by using the interference signal IS that has been detected by the interference light detection means 40 for each scan line, and obtains a tomographic image P of the measurement target S by using the tomographic information r(z). Further, the probe outer-tube 11 of the optical probe 10 has the light-transmitting area PR and the light-blocking area SR. The light-transmitting area PR is formed along a rotation direction R1 of the optical fiber 12 and transmits the light output from the leading-end optical system 15. The light-blocking area SR is formed at the start position and the end position of the light-transmitting area PR, and blocks the light output from the leading-end optical system 15. The tomographic image processing means 50 includes the interference signal analysis means 53, the light-blocking-area detection means 55, the light-transmitting-area detection means 56, and the tomographic image production means 54. The interference signal analysis means 53 obtains, based on the interference signal IS detected by the interference light detection means 40, tomographic information r (z) about the measurement target S for each scan line, thereby obtaining a plurality of pieces of tomographic information. The light-blocking-area detection means 55 detects at least one light-blocking interference signal ISS or piece of light-blocking tomographic information rs(z) that has been obtained in the light-blocking area SR in the plurality of interference signals IS or the plurality of pieces of tomographic information r(z), respectively. The light-transmitting-area detection means 56 detects interference signals IS or pieces of tomographic information obtained in the light-transmitting area by using the at least one light-blocking interference signal ISS or piece of light-blocking tomographic information rs(z) that has been detected by the light-blocking-area detection means 55, respectively. The tomographic image production means 54 produces the tomographic image P of the light-transmitting area PR by using the interference signals IS or the pieces of tomographic information obtained in the light-transmitting area PR, which has been detected by the light-transmitting-area detection means 56. Therefore, the tomographic image P is produced by identifying the interference signals IS or pieces of the tomographic information obtained in the light-transmitting area in the plurality of interference signals or the plurality of pieces of tomographic information r(z) that are obtained for each scan line. Hence, even if the rotation becomes irregular, it is possible to produce the tomographic image P in the light-transmitting area PR by using the interference signals IS when the light-transmitting area PR is irradiated with the measurement light L1. Hence, it is possible to prevent deterioration in the image quality of the tomographic image due to irregular rotation of the leading-end optical system 15.

Further, when the light-blocking area SR reflects the measurement light that has been output from the leading-end optical system 15 toward the leading-end optical system 15 side, and the light-blocking-area detection means 55 detects the light-blocking area SR by judging whether the signal level of the interference signal IS exceeds a predetermined threshold value, the light-transmitting area PR can be detected without performing spectral analysis on the interference signal IS. Therefore, it is possible to perform efficient tomographic image processing.

Further, when the light-blocking area SR absorbs or scatters the measurement light that has been output from the leading-end optical system, and the light-blocking-area detection means 55 detects the light-blocking area SR by judging whether the signal level of the interference signal IS is lower than a predetermined threshold value, the light-transmitting area PR can be detected without performing spectral analysis on the interference signal IS. Therefore, it is possible to perform efficient tomographic image processing.

Further, when the light-blocking area SR reflects the measurement light L1 that has been output from the leading-end optical system 15 toward the leading-end optical system 15 side, and the light-blocking-area detection means 55 detects the light-blocking area SR by judging whether the tomographic information r(zh) that corresponds to the position of the probe outer-tube 11 exceeds a predetermined threshold value, it is possible to accurately detect the light-transmitting area PR.

Further, when the light-blocking area SR absorbs or scatters the measurement light that has been output from the leading-end optical system 15, and the light-blocking-area detection means 55 detects the light-blocking area SR by judging whether the tomographic information that corresponds to the position of the probe outer-tube 11 is lower than a predetermined threshold value, it is possible to accurately detect the light-transmitting area PR.

Further, the tomographic image production means 54 thins scan lines constituting the light-transmitting area PR detected by the light-transmitting-area detection means 56 so that the number of the scan lines becomes a set number when the number of the scan lines exceeds the set number. The tomographic image production means 54 interpolates a scan line or scan lines in the light-transmitting area PR so that the number of the scan lines becomes the set number when the number of the scan lines is smaller than the set number. If the tomographic image production means 54 thins the scan lines or interpolates the scan line or scan lines as described above, when the tomographic image in the light-transmitting area PR is displayed as motion image (dynamic image or video image) by repeating scanning with the measurement light L1, it is possible to display a tomographic image in such a manner that consecutive image frames of the motion image have substantially the same image quality.

Figure 11:
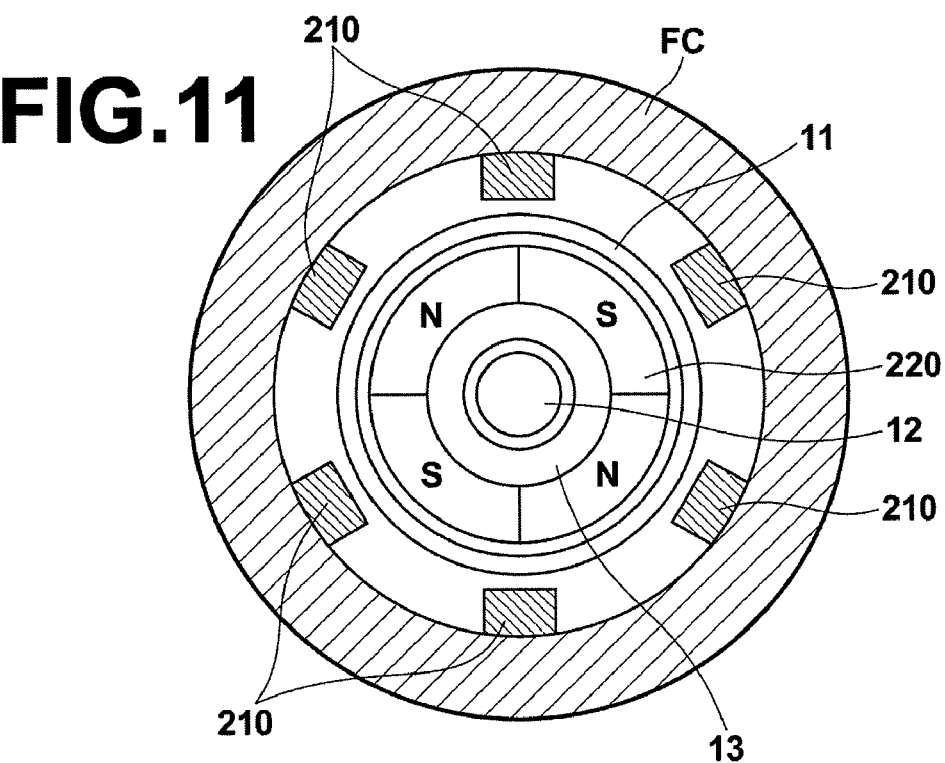
FIG. 11 is a schematic diagram illustrating a rotation detection mechanism provided in a forceps channel of an endoscope.

The embodiments of the present invention are not limited to the aforementioned embodiments. For example, as illustrated in FIG. 11, the irradiation position with the measurement light L1 may be detected by a rotation detection mechanism that is built in forceps channel FC, in addition to detecting the light-transmitting area PR based on the light-blocking area SR. In FIG. 11, a plurality of hall IC's 210 are attached to the forceps channel FC side, and a disk-shaped magnet 220 is provided within the probe outer-tube 11. The hall IC 210 detects magnetism (a magnetic field), thereby detecting the direction of the leading-end optical system 15 (irradiation position with the measurement light L1). For example, the hall IC 210 may be provided at a phase portion corresponding to each of the start position SRS and the end position SRE of the light-transmitting area PR. If the hall IC 210 is provided in such a manner, it is possible to improve the accuracy in detecting the start position SRS and the end position SRE.

Figure 12:
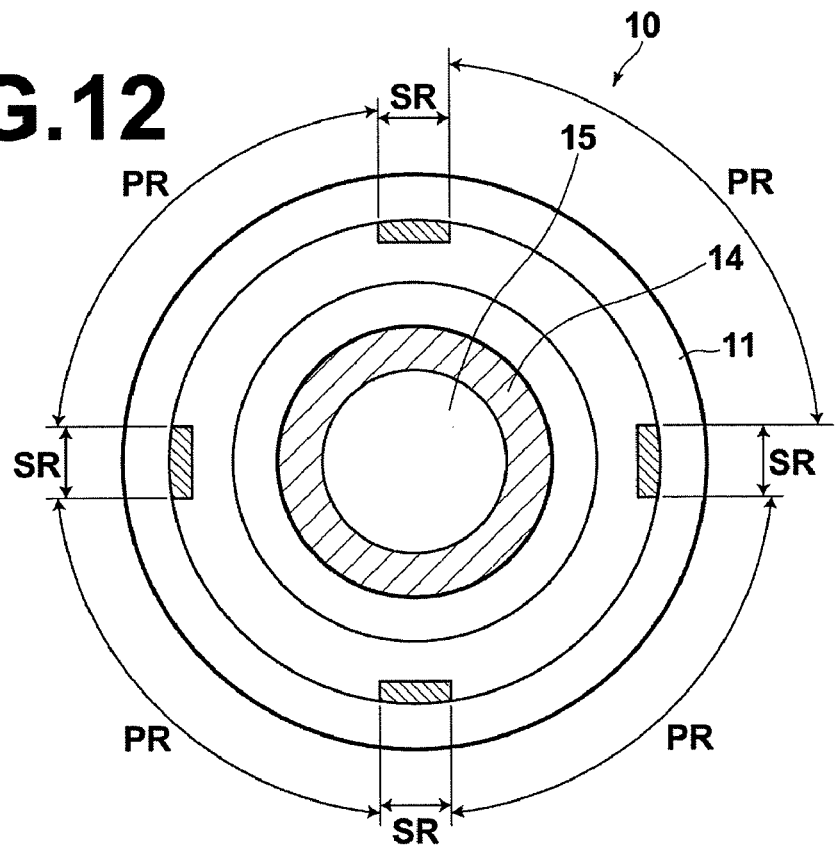
FIG. 12 is a schematic diagram illustrating another embodiment of the optical probe according to the present invention.

Further, for example, in the optical probe illustrated in FIGS. 5 and 9, a single light-transmitting area PR is formed. However, a plurality of light-transmitting areas PR may be formed. In other words, when at least two light-blocking areas SR are formed along the scan direction, it is possible to detect a light-transmitting area PR between the two light-blocking areas SR. For example, as illustrated in FIG. 12, four light-transmitting areas PR and four light-blocking areas SR may be formed.

Further, in the optical tomographic image production apparatus 1 illustrated in FIG. 2, a case in which the tomographic image P is obtained by so-called SS-OCT measurement is illustrated. Alternatively, the optical tomographic image production apparatus 1 may be applied to an optical probe of an optical tomographic image production apparatus that obtains the tomographic image by SD-OCT measurement or TD-OCT measurement by rotationally scanning the target.

What is claimed is:

1. An optical tomographic image production apparatus comprising:
   a light source unit that emits light;
   a light division means that divides the light emitted from the light source unit into measurement light and reference light;
   an optical probe comprising:
      a probe outer-tube that has substantially cylindrical form, and which is inserted into a subject to be examined;
      an optical fiber that is arranged in the inner space of the probe outer-tube in the longitudinal direction thereof; and
      a leading-end optical system that is rotatable with respect to the probe outer-tube, and which deflects light output from the leading end of the optical fiber toward a measurement target in the subject to be examined, wherein an outer peripheral portion of the probe outer-tube has-a corresponding to the leading end optical system comprises at least one light-transmitting area that transmits the light output from the leading end optical system and at least one a-light-blocking area that defines a start position and an end position of the light transmitting region; and
      the at least one light transmitting area and the at least one light blocking area are provided such that the optical path of the light output by the leading end optical system intersects with the boundary between the light transmitting area and the light blocking area, when the leading end optical system is rotated;
   a light combination means that combines reflection light and the reference light, the reflection light being reflected from the measurement target when the measurement target is irradiated with the measurement light, which has been guided by the optical probe, in such a manner to scan the measurement target;
   an interference light detection means that detects, as an interference signal, interference light of the reflection light and the reference light that have been combined by the light combination means for each scan line, thereby detecting a plurality of interference signals; and
   a tomographic image processing means that obtains tomographic information about the measurement target by using the interference signal that has been detected by the interference light detection means for each scan line, and obtains a tomographic image of the measurement target by using the tomographic information, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means, wherein the light-blocking area reflects the measurement light that has been output from the leading-end optical system toward the leading-end optical system side, and wherein the light-blocking-area detection means detects the light-blocking area by judging whether the signal level of each of the interference signals exceeds a predetermined threshold value.

2. An optical tomographic image production apparatus comprising:
   a light source unit that emits light;
   a light division means that divides the light emitted from the light source unit into measurement light and reference light;
   an optical probe comprising:
      a probe outer-tube that has substantially cylindrical form, and which is inserted into a subject to be examined;
      an optical fiber that is arranged in the inner space of the probe outer-tube in the longitudinal direction thereof; and
      a leading-end optical system that is rotatable with respect to the probe outer-tube, and which deflects light output from the leading end of the optical fiber toward a measurement target in the subject to be examined, wherein an outer peripheral portion of the probe outer-tube has-a corresponding to the leading end optical system comprises at least one light-transmitting area that transmits the light output from the leading end optical system and at least one a-light-blocking area that defines a start position and an end position of the light transmitting region; and
      the at least one light transmitting area and the at least one light blocking area are provided such that the optical path of the light output by the leading end optical system intersects with the boundary between the light transmitting area and the light blocking area, when the leading end optical system is rotated;
   a light combination means that combines reflection light and the reference light, the reflection light being reflected from the measurement target when the measurement target is irradiated with the measurement light, which has been guided by the optical probe, in such a manner to scan the measurement target;
   an interference light detection means that detects, as an interference signal, interference light of the reflection light and the reference light that have been combined by the light combination means for each scan line, thereby detecting a plurality of interference signals; and
   a tomographic image processing means that obtains tomographic information about the measurement target by using the interference signal that has been detected by the interference light detection means for each scan line, and obtains a tomographic image of the measurement target by using the tomographic information, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means, wherein the light-blocking area absorbs or scatters the measurement light that has been output from the leading-end optical system, and wherein the light-blocking-area detection means detects the light-blocking area by judging whether the signal level of each of the interference signals is lower than a predetermined threshold value.

3. An optical tomographic image production apparatus comprising:
   a light source unit that emits light;
   a light division means that divides the light emitted from the light source unit into measurement light and reference light;
   an optical probe comprising:
      a probe outer-tube that has substantially cylindrical form, and which is inserted into a subject to be examined;
      an optical fiber that is arranged in the inner space of the probe outer-tube in the longitudinal direction thereof; and
      a leading-end optical system that is rotatable with respect to the probe outer-tube, and which deflects light output from the leading end of the optical fiber toward a measurement target in the subject to be examined, wherein an outer peripheral portion of the probe outer-tube has-a corresponding to the leading end optical system comprises at least one light-transmitting area that transmits the light output from the leading end optical system and at least one a-light-blocking area that defines a start position and an end position of the light transmitting region; and
      the at least one light transmitting area and the at least one light blocking area are provided such that the optical path of the light output by the leading end optical system intersects with the boundary between the light transmitting area and the light blocking area, when the leading end optical system is rotated;

a light combination means that combines reflection light and the reference light, the reflection light being reflected from the measurement target when the measurement target is irradiated with the measurement light, which has been guided by the optical probe, in such a manner to scan the measurement target;

an interference light detection means that detects, as an interference signal, interference light of the reflection light and the reference light that have been combined by the light combination means for each scan line, thereby detecting a plurality of interference signals; and a tomographic image processing means that obtains tomographic information about the measurement target by using the interference signal that has been detected by the interference light detection means for each scan line, and obtains a tomographic image of the measurement target by using the tomographic information, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means, wherein the light-blocking area reflects the measurement light that has been output from the leading-end optical system toward the leading-end optical system side, and wherein the light-blocking-area detection means detects the light-blocking area by judging whether the tomographic information that corresponds to the position of the probe outer-tube exceeds a predetermined threshold value.

4. An optical tomographic image production apparatus comprising:
a light source unit that emits light;
a light division means that divides the light emitted from the light source unit into measurement light and reference light;
an optical probe comprising:
a probe outer-tube that has substantially cylindrical form, and which is inserted into a subject to be examined;
an optical fiber that is arranged in the inner space of the probe outer-tube in the longitudinal direction thereof; and
a leading-end optical system that is rotatable with respect to the probe outer-tube, and which deflects light output from the leading end of the optical fiber toward a measurement target in the subject to be examined, wherein an outer peripheral portion of the probe outer-tube has-a corresponding to the leading end optical system comprises at least one light-transmitting area that transmits the light output from the leading end optical system and at least one a-light-blocking area that defines a start position and an end position of the light transmitting region; and
the at least one light transmitting area and the at least one light blocking area are provided such that the optical path of the light output by the leading end optical system intersects with the boundary between the light transmitting area and the light blocking area, when the leading end optical system is rotated;
a light combination means that combines reflection light and the reference light, the reflection light being reflected from the measurement target when the measurement target is irradiated with the measurement light, which has been guided by the optical probe, in such a manner to scan the measurement target;
an interference light detection means that detects, as an interference signal, interference light of the reflection light and the reference light that have been combined by the light combination means for each scan line, thereby detecting a plurality of interference signals; and
a tomographic image processing means that obtains tomographic information about the measurement target by using the interference signal that has been detected by the interference light detection means for each scan line, and obtains a tomographic image of the measurement target by using the tomographic information, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means, wherein the light-blocking area absorbs or scatters the measurement light that has been output from the leading-end optical system, and wherein the light-blockingarea detection means detects the light-blocking area by judging whether the tomographic information that corresponds to the position of the probe outer-tube is lower than a predetermined threshold value.

5. An optical tomographic image production apparatus, comprising:

a light source unit that emits light;

a light division means that divides the light emitted from the light source unit into measurement light and reference light;

an optical probe comprising:
- a probe outer-tube that has substantially cylindrical form, and which is inserted into a subject to be examined;
- an optical fiber that is arranged in the inner space of the probe outer-tube in the longitudinal direction thereof; and
- a leading-end optical system that is rotatable with respect to the probe outer-tube, and which deflects light output from the leading end of the optical fiber toward a measurement target in the subject to be examined, wherein an outer peripheral portion of the probe outer-tube has-a corresponding to the leading end optical system comprises at least one light-transmitting area that transmits the light output from the leading end optical system and at least one a-light-blocking area that defines a start position and an end position of the light transmitting region; and
- the at least one light transmitting area and the at least one light blocking area are provided such that the optical path of the light output by the leading end optical system intersects with the boundary between the light transmitting area and the light blocking area, when the leading end optical system is rotated;

a light combination means that combines reflection light and the reference light, the reflection light being reflected from the measurement target when the measurement target is irradiated with the measurement light, which has been guided by the optical probe, in such a manner to scan the measurement target;

an interference light detection means that detects, as an interference signal, interference light of the reflection light and the reference light that have been combined by the light combination means for each scan line, thereby detecting a plurality of interference signals; and a tomographic image processing means that obtains tomographic information about the measurement target by using the interference signal that has been detected by the interference light detection means for each scan line, and obtains a tomographic image of the measurement target by using the tomographic information, wherein the tomographic image processing means includes an interference signal analysis means, a light-blocking-area detection means, a light-transmitting-area detection means, and a tomographic image production means, and wherein the interference signal analysis means obtains, based on the interference signal detected by the interference light detection means, tomographic information about the measurement target for each scan line, thereby obtaining a plurality of pieces of tomographic information, and wherein the light-blocking-area detection means detects at least one light-blocking interference signal or piece of light-blocking tomographic information that has been obtained in the light-blocking area in the plurality of interference signals or the plurality of pieces of tomographic information, respectively, and wherein the light-transmitting-area detection means detects interference signals or pieces of tomographic information obtained in the light-transmitting area by using the at least one light-blocking interference signal or piece of light-blocking tomographic information that has been detected by the light-blocking-area detection means, respectively, and wherein the tomographic image production means produces a tomographic image of the light-transmitting area by using the interference signals or the pieces of tomographic information obtained in the light-transmitting area, which have been detected by the light-transmitting-area detection means, wherein the tomographic image production means thins scan lines constituting the light-transmitting area detected by the light-transmitting-area detection means so that the number of the scan lines becomes a set number when the number of the scan lines exceeds the set number, and wherein the tomographic image production means interpolates a scan line or scan lines in the light-transmitting area so that the number of the scan lines becomes the set number when the number of the scan lines is smaller than the set number.

* * * * *